United States Patent [19]

Stein et al.

[11] Patent Number: 6,074,862
[45] Date of Patent: *Jun. 13, 2000

[54] MITOGEN-ACTIVATED PROTEIN KINASE KINASE MEK6 AND VARIANTS THEREOF

[75] Inventors: Bernd Stein; Maria X. H. Yang, both of San Diego, Calif.

[73] Assignee: Signal Pharmaceuticals Inc., San Diego, Calif.

[21] Appl. No.: 08/576,240

[22] Filed: Dec. 20, 1995

[51] Int. Cl.$^7$ ...................................................... C12N 9/12
[52] U.S. Cl. ........................ 435/194; 530/350; 424/94.1
[58] Field of Search ........................... 530/350; 435/194; 424/91.1

[56] References Cited

U.S. PATENT DOCUMENTS 5,736,381   4/1998   Davis et al. ........................... 435/252.3

FOREIGN PATENT DOCUMENTS

WO 95/21923   8/1995   WIPO.
WO 96/36642   11/1996  WIPO.

OTHER PUBLICATIONS

Raingeaud et al., Mol. Cell. Biol., 16(3): 1247–1255, Mar. 1996.
Darnel et al., Molecular Cell Biology, Scientific American Books: New York, NY, p. 54, 1986.
Han et al., "A MAP Kinase Targeted by Endotoxin and Hypersmolarity in Mammalian Cells," *Science* 265: 808–811, 1994.
Dérijard et al., "Independent Human MAP Kinase Signal Transduction Pathways Defined by MEK and MKK Isoforms," *Science* 267: 682–685, 1995.
Yashar et al., "Novel Members of the Mitogen–Activated Protein Kinase Activator Family in *Xenopus laevis*," *Molecular and Cellular Biology* 13(9); 5738–5748, 1993.
Cano and Mahadevan, "Parallel signal processing among mammalian MAPKs," *Trends in Biochemical Sciences* 20: 117–122, 1995.
Lee et al., "A protein kinase involved in the regulation of inflammatory cytokine biosynthesis," *Nature* 372: 739–746, 1994.
Lin et al., "Identification of a Dual Specificity Kinase That Activates the Jun Kinases and p38–Mpk2," *Science* 268: 286–290, 1995.
Herskowitz, I., "MAP Kinase Pathways in Yeast: For Mating and More," *Cell 80*: 187–197, 1995.
Yan et al., "Activation of stress–activated protein kinase by MEKK1 phosphorylation of its activator SEK1," *Nature* 372: 798–800, 1994.
Seger and Krebs, "The MAPK signaling cascade," *FASEB Journal* 9: 726–735, 1995.
Rouse et al., "A Novel Kinase Cascade Triggered by Stress and Heat Shock That Stimulates MAPKAP Kinase–2 and Phosphorylation of the Small Heat Shock Proteins," *Cell* 78: 1027–1037, 1994.

Pang et al., "Inhibition of MAP Kinase Kinase Blocks the Differentiation of PC–12 Cells Induced by Nerve Growth Factor," *Journal of Biological Chemistry* 270(23): 13585–13588, 1995.
Moriguchi et al., "Evidence for Multiple Activators for Stress–activated Protein Kinases/c–Jun Amino–terminal Kinases. Existence of Novel Activators," *Journal of Biological Chemistry* 270(22): 12969–12972, 1995.
Davis, r. "MAPKs: new JNk expands the group," *Trends in Biochemical Sciences 19*: 470–473, 1994.
Minden et al., "Differential Activation of ERK and JNK Mitogen–Activated Protein Kinases by Raf–1 and MEKK," *Science* 266: 1719–1723, 1994.
Cobb et al., "Extracellular signal–regulated kinases; ERKs in progress," *Cell Regulation* 2: 965–978, 1991.
Zhou et al., "Components of a New Human Protein Kinase Signal Transduction Pathway," *Journal of Biological Chemistry* 270(21): 12665–12669, 1995.
Cobb and Goldsmith, "How MAP Kinases Are Regulated," *Journal of Biological Chemistry* 270(25): 14843–14846, 1995.
Hunter and Karin, "The Regulation of Transcription by Phosphorylation," *Cell* 70: 375–387, 1992.
Hunter, T., "Protein Kinases and Phosphatases: The Yin and Yang of Protein Phosphorylation and Signalig," *Cell 80*: 225–236, 1995.
Karin and Smeal, "Control of transcription factors by signal transduction pathways: the beginning of the end," *Trends in Biochemical Sciences 17*: 418–422, 1992.
Sánchez et al., "Role of SAPK/ERK kinase–1 in the stress–activated pathway regulating transcription factor c–Jun," *Nature* 372: 794–798, 1994.
Crystal, R. Science. vol. 270: pp. 404–410, Oct. 20, 1995.
Cuenda et al., "Purification and cDNa cloning of SAPKK3, the major activator of RK/p38 in stress–and cytokine–stimulated monocytes and epithelial cells," *EMBO Journal* 15(16): 4156–4164, 1996.
Han et al., "Characterization of the Structure and Function of a Novel MAP Kinase Kinase (MKK6)," *Journal of Biological Chemistry* 271(6): 2886–2891, 1996.
Stein et al., "Cloning and Characterization of MEK6, a Novel Member of the Mitogen–activated Protein Kinase Kinase Cascade," *Journal of Biological Chemistry* 271(19): 11427–11423, 1996.

*Primary Examiner*—Lila Feisee
*Assistant Examiner*—Claire M. Kaufman
*Attorney, Agent, or Firm*—Seed and Berry LLP

[57] ABSTRACT

Compositions and methods are provide for potentiating the activity of the mitogen-activated protein kinase p38. In particular the mitogen-activated protein kinase kinase MEK6, and variants thereof that stimulate phosphorylation of p38 are provided. Such compounds may be used, for example, for therapy of diseases associated with the p38 cascade and to identify antibodies and other agents that inhibit or activate signal transduction via p38.

2 Claims, 10 Drawing Sheets hMEK6 NUCLEOTIDE AND AMINO ACID SEQUENCES

```
ATG TCT CAG TCG AAA GGC AAG AAG CGA AAC CCT GGC CTT AAA ATT CCA    48
 M   S   Q   S   K   G   K   K   R   N   P   G   L   K   I   P
 1           5                   10                  15

AAA GAA GCA TTT GAA CAA CCT CAG ACC AGT TCC ACA CCA CCT CGA GAT    96
 K   E   A   F   E   Q   P   Q   T   S   S   T   P   P   R   D
                 20                  25                  30

TTA GAC TCC AAG GCT TGC ATT TCT ATT GGA AAT CAG AAC TTT GAG GTG   144
 L   D   S   K   A   C   I   S   I   G   N   Q   N   F   E   V
             35                  40                  45

AAG GCA GAT GAC CTG GAG CCT ATA ATG GAA CTG GGA CGA GGT GCG TAC   192
 K   A   D   D   L   E   P   I   M   E   L   G   R   G   A   Y
         50                  55                  60

GGG GTG GTG GAG AAG ATG CGG CAC GTG CCC AGC GGG CAG ATC ATG GCA   240
 G   V   V   E   K   M   R   H   V   P   S   G   Q   I   M   A
 65              70                  75                  80

GTG AAG CGG ATC CGA GCC ACA GTA AAT AGC CAG GAA CAG AAA CGG CTA   288
 V   K   R   I   R   A   T   V   N   S   Q   E   Q   K   R   L
                     85                  90                  95

CTG ATG GAT TTG GAT ATT TCC ATG AGG ACG GTG GAC TGT CCA TTC ACT   336
 L   M   D   L   D   I   S   M   R   T   V   D   C   P   F   T
                 100                 105                 110

GTC ACC TTT TAT GGC GCA CTG TTT CGG GAG GGT GAT GTG TGG ATC TGC   384
 V   T   F   Y   G   A   L   F   R   E   G   D   V   W   I   C
             115                 120                 125

ATG GAG CTC ATG GAT ACA TCA CTA GAT AAA TTC TAC AAA CAA GTT ATT   432
 M   E   L   M   D   T   S   L   D   K   F   Y   K   Q   V   I
         130                 135                 140

GAT AAA GGC CAG ACA ATT CCA GAG GAC ATC TTA GGG AAA ATA GCA GTT   480
 D   K   G   Q   T   I   P   E   D   I   L   G   K   I   A   V
 145                 150                 155                 160

TCT ATT GTA AAA GCA TTA GAA CAT TTA CAT AGT AAG CTG TCT GTC ATT   528
 S   I   V   K   A   L   E   H   L   H   S   K   L   S   V   I
                     165                 170                 175
```

*Fig. 1-1* hMEK6 NUCLEOTIDE AND AMINO ACID SEQUENCES

| CAC | AGA | GAC | GTC | AAG | CCT | TCT | AAT | GTA | CTC | ATC | AAT | GCT | CTC | GGT | CAA | 576 |
| H | R | D | V | K | P | S | N | V | L | I | N | A | L | G | Q | |
| | | | 180 | | | | | 185 | | | | | 190 | | | |

| GTG | AAG | ATG | TGC | GAT | TTT | GGA | ATC | AGT | GGC | TAC | TTG | GTG | GAC | TCT | GTT | 624 |
| V | K | M | C | D | F | G | I | S | G | Y | L | V | D | S | V | |
| | | 195 | | | | | 200 | | | | | 205 | | | | |

| GCT | AAA | ACA | ATT | GAT | GCA | GGT | TGC | AAA | CCA | TAC | ATG | GCC | CCT | GAA | AGA | 672 |
| A | K | T | I | D | A | G | C | K | P | Y | M | A | P | E | R | |
| | 210 | | | | | 215 | | | | | 220 | | | | | |

| ATA | AAC | CCA | GAG | CTC | AAC | CAG | AAG | GGA | TAC | AGT | GTG | AAG | TCT | GAC | ATT | 720 |
| I | N | P | E | L | N | Q | K | G | Y | S | V | K | S | D | I | |
| 225 | | | | | 230 | | | | | 235 | | | | | 240 | |

| TGG | AGT | CTG | GGC | ATC | ACG | ATG | ATT | GAG | TTG | GCC | ATC | CTT | CGA | TTT | CCC | 768 |
| W | S | L | G | I | T | M | I | E | L | A | I | L | R | F | P | |
| | | | | 245 | | | | | 250 | | | | | 255 | | |

| TAT | GAT | TCA | TGG | GGA | ACT | CCA | TTT | CAG | CAG | CTC | AAA | CAG | GTG | GTA | GAG | 816 |
| Y | D | S | W | G | T | P | F | Q | Q | L | K | Q | V | V | E | |
| | | | | 260 | | | | | 265 | | | | | 270 | | |

| GAG | CCA | TCG | CCA | CAA | CTC | CCA | GCA | GAC | AAG | TTC | TCT | GCA | GAG | TTT | GTT | 864 |
| E | P | S | P | Q | L | P | A | D | K | F | S | A | E | F | V | |
| | | 275 | | | | | 280 | | | | | 285 | | | | |

| GAC | TTT | ACC | TCA | CAG | TGC | TTA | AAG | AAG | AAT | TCC | AAA | GAA | CGG | CCT | ACA | 912 |
| D | F | T | S | Q | C | L | K | K | N | S | K | E | R | P | T | |
| | 290 | | | | | 295 | | | | | 300 | | | | | |

| TAC | CCA | GAG | CTA | ATG | CAA | CAT | CCA | TTT | TTC | ACC | CTA | CAT | GAA | TCC | AAA | 960 |
| Y | P | E | L | M | Q | H | P | F | F | T | L | H | E | S | K | |
| 305 | | | | | 310 | | | | | 315 | | | | | 320 | |

| GGA | ACA | GAT | GTG | GCA | TCT | TTT | GTA | AAA | CTG | ATT | CTT | GGA | GAC | | | 1002 |
| G | T | D | V | A | S | F | V | K | L | I | L | G | D | | | |
| | | | | 325 | | | | | 330 | | | | | | | |

*Fig. 1-2*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1002 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1002

(xi) SEQUENCE DESCRIPTION: SEQ ID NO:1:

```
ATG TCT CAG TCG AAA GGC AAG AAG CGA AAC CCT GGC CTT AAA ATT CCA        48
Met Ser Gln Ser Lys Gly Lys Lys Arg Asn Pro Gly Leu Lys Ile Pro
 1               5                  10                  15

AAA GAA GCA TTT GAA CAA CCT CAG ACC AGT TCC ACA CCA CCT CGA GAT        96
Lys Glu Ala Phe Glu Gln Pro Gln Thr Ser Ser Thr Pro Pro Arg Asp
                20                  25                  30

TTA GAC TCC AAG GCT TGC ATT TCT ATT GGA AAT CAG AAC TTT GAG GTG       144
Leu Asp Ser Lys Ala Cys Ile Ser Ile Gly Asn Gln Asn Phe Glu Val
            35                  40                  45

AAG GCA GAT GAC CTG GAG CCT ATA ATG GAA CTG GGA CGA GGT GCG TAC       192
Lys Ala Asp Asp Leu Glu Pro Ile Met Glu Leu Gly Arg Gly Ala Tyr
        50                  55                  60

GGG GTG GTG GAG AAG ATG CGG CAC GTG CCC AGC GGG CAG ATC ATG GCA       240
Gly Val Val Glu Lys Met Arg His Val Pro Ser Gly Gln Ile Met Ala
 65                  70                  75                  80

GTG AAG CGG ATC CGA GCC ACA GTA AAT AGC CAG GAA CAG AAA CGG CTA       288
Val Lys Arg Ile Arg Ala Thr Val Asn Ser Gln Glu Gln Lys Arg Leu
                85                  90                  95

CTG ATG GAT TTG GAT ATT TCC ATG AGG ACG GTG GAC TGT CCA TTC ACT       336
Leu Met Asp Leu Asp Ile Ser Met Arg Thr Val Asp Cys Pro Phe Thr
                100                 105                 110
```

```
GTC ACC TTT TAT GGC GCA CTG TTT CGG GAG GGT GAT GTG TGG ATC TGC      384
Val Thr Phe Tyr Gly Ala Leu Phe Arg Glu Gly Asp Val Trp Ile Cys
        115                 120                 125

ATG GAG CTC ATG GAT ACA TCA CTA GAT AAA TTC TAC AAA CAA GTT ATT      432
Met Glu Leu Met Asp Thr Ser Leu Asp Lys Phe Tyr Lys Gln Val Ile
130                 135                 140

GAT AAA GGC CAG ACA ATT CCA GAG GAC ATC TTA GGG AAA ATA GCA GTT      480
Asp Lys Gly Gln Thr Ile Pro Glu Asp Ile Leu Gly Lys Ile Ala Val
145                 150                 155                 160

TCT ATT GTA AAA GCA TTA GAA CAT TTA CAT AGT AAG CTG TCT GTC ATT      528
Ser Ile Val Lys Ala Leu Glu His Leu His Ser Lys Leu Ser Val Ile
                165                 170                 175

CAC AGA GAC GTC AAG CCT TCT AAT GTA CTC ATC AAT GCT CTC GGT CAA      576
His Arg Asp Val Lys Pro Ser Asn Val Leu Ile Asn Ala Leu Gly Gln
            180                 185                 190

GTG AAG ATG TGC GAT TTT GGA ATC AGT GGC TAC TTG GTG GAC TCT GTT      624
Val Lys Met Cys Asp Phe Gly Ile Ser Gly Tyr Leu Val Asp Ser Val
        195                 200                 205

GCT AAA ACA ATT GAT GCA GGT TGC AAA CCA TAC ATG GCC CCT GAA AGA      672
Ala Lys Thr Ile Asp Ala Gly Cys Lys Pro Tyr Met Ala Pro Glu Arg
    210                 215                 220

ATA AAC CCA GAG CTC AAC CAG AAG GGA TAC AGT GTG AAG TCT GAC ATT      720
Ile Asn Pro Glu Leu Asn Gln Lys Gly Tyr Ser Val Lys Ser Asp Ile
225                 230                 235                 240

TGG AGT CTG GGC ATC ACG ATG ATT GAG TTG GCC ATC CTT CGA TTT CCC      768
Trp Ser Leu Gly Ile Thr Met Ile Glu Leu Ala Ile Leu Arg Phe Pro
                245                 250                 255

TAT GAT TCA TGG GGA ACT CCA TTT CAG CAG CTC AAA CAG GTG GTA GAG      816
Tyr Asp Ser Trp Gly Thr Pro Phe Gln Gln Leu Lys Gln Val Val Glu
            260                 265                 270

GAG CCA TCG CCA CAA CTC CCA GCA GAC AAG TTC TCT GCA GAG TTT GTT      864
Glu Pro Ser Pro Gln Leu Pro Ala Asp Lys Phe Ser Ala Glu Phe Val
        275                 280                 285

GAC TTT ACC TCA CAG TGC TTA AAG AAG AAT TCC AAA GAA CGG CCT ACA      912
Asp Phe Thr Ser Gln Cys Leu Lys Lys Asn Ser Lys Glu Arg Pro Thr
    290                 295                 300

TAC CCA GAG CTA ATG CAA CAT CCA TTT TTC ACC CTA CAT GAA TCC AAA      960
Tyr Pro Glu Leu Met Gln His Pro Phe Phe Thr Leu His Glu Ser Lys
305                 310                 315                 320

GGA ACA GAT GTG GCA TCT TTT GTA AAA CTG ATT CTT GGA GAC                1002
Gly Thr Asp Val Ala Ser Phe Val Lys Leu Ile Leu Gly Asp
                325                 330
```

(2) INFORMATION FOR SEQ ID NO:2:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Gln Ser Lys Gly Lys Lys Arg Asn Pro Gly Leu Lys Ile Pro
1               5                   10                  15

Lys Glu Ala Phe Glu Gln Pro Gln Thr Ser Ser Thr Pro Pro Arg Asp
            20                  25                  30

Leu Asp Ser Lys Ala Cys Ile Ser Ile Gly Asn Gln Asn Phe Glu Val
        35                  40                  45

Lys Ala Asp Asp Leu Glu Pro Ile Met Glu Leu Gly Arg Gly Ala Tyr
```

```
            50                  55                  60
Gly Val Val Glu Lys Met Arg His Val Pro Ser Gly Gln Ile Met Ala
65                  70                  75                  80

Val Lys Arg Ile Arg Ala Thr Val Asn Ser Gln Glu Gln Lys Arg Leu
                85                  90                  95

Leu Met Asp Leu Asp Ile Ser Met Arg Thr Val Asp Cys Pro Phe Thr
                100                 105                 110

Val Thr Phe Tyr Gly Ala Leu Phe Arg Glu Gly Asp Val Trp Ile Cys
            115                 120                 125

Met Glu Leu Met Asp Thr Ser Leu Asp Lys Phe Tyr Lys Gln Val Ile
        130                 135                 140

Asp Lys Gly Gln Thr Ile Pro Glu Asp Ile Leu Gly Lys Ile Ala Val
145                 150                 155                 160

Ser Ile Val Lys Ala Leu Glu His Leu His Ser Lys Leu Ser Val Ile
                165                 170                 175

His Arg Asp Val Lys Pro Ser Asn Val Leu Ile Asn Ala Leu Gly Gln
                180                 185                 190

Val Lys Met Cys Asp Phe Gly Ile Ser Gly Tyr Leu Val Asp Ser Val
            195                 200                 205

Ala Lys Thr Ile Asp Ala Gly Cys Lys Pro Tyr Met Ala Pro Glu Arg
        210                 215                 220

Ile Asn Pro Glu Leu Asn Gln Lys Gly Tyr Ser Val Lys Ser Asp Ile
225                 230                 235                 240

Trp Ser Leu Gly Ile Thr Met Ile Glu Leu Ala Ile Leu Arg Phe Pro
                245                 250                 255

Tyr Asp Ser Trp Gly Thr Pro Phe Gln Gln Leu Lys Gln Val Val Glu
                260                 265                 270

Glu Pro Ser Pro Gln Leu Pro Ala Asp Lys Phe Ser Ala Glu Phe Val
            275                 280                 285

Asp Phe Thr Ser Gln Cys Leu Lys Lys Asn Ser Lys Glu Arg Pro Thr
        290                 295                 300

Tyr Pro Glu Leu Met Gln His Pro Phe Phe Thr Leu His Glu Ser Lys
305                 310                 315                 320

Gly Thr Asp Val Ala Ser Phe Val Lys Leu Ile Leu Gly Asp
                325                 330
```

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:3:

TTGTGCTCCC CTCCCCCATC AAAGGAA                                27

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:4:

CACATCTTCA CTTGACCGAG AGCA                                  24

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

CCAACCATGG CTCAGGAGAG                                      20

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:6:

CGGTACCTTC AGGACTCCAT CT                                   22

MITOGEN-ACTIVATED PROTEIN KINASE KINASE MEK6 AND VARIANTS THEREOF

TECHNICAL FIELD

The present invention relates generally to compositions and methods for modulating the activity of the mitogen-activated protein kinases, including p38. The invention is more particularly related to the mitogen-activated protein kinase kinase MEK6 and variants thereof that stimulate phosphorylation and activation of substrates, such as p38, and to the use of compounds, for example, to activate p38 and to identify antibodies and other agents that inhibit or activate signal transduction via the p38 kinase cascade.

BACKGROUND OF THE INVENTION

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif with the sequence Thr-X-Tyr by mitogen-activated protein kinase kinases (MAPKKs). In higher eukaryotes, the physiological role of MAPK signaling has been correlated with cellular events such as proliferation, oncogenesis, development and differentiation. Accordingly, the ability to regulate signal transduction via these pathways could lead to the development of treatments and preventive therapies for human diseases associated with MAPK signaling, such as inflammatory diseases, autoimmune diseases and cancer.

In mammalian cells, three parallel MAPK pathways have been described. The best characterized pathway leads to the activation of the extracellular-signal-regulated kinase (ERK). Less well understood are the signal transduction pathways leading to the activation of the cJun N-terminal kinase (JNK) and the p38 MAPK (for reviews, see Davis, *Trends Biochem. Sci.* 19:470–473 (1994); Cano and Mahadevan, *Trends Biochem. Sci.* 20:117–122(1995)). The identification and characterization of members of these cascades is critical for understanding the signal transduction pathways involved and for developing methods for activating or inactivating MAPKs in vivo.

Two MAPKKs capable of activating p38 in vitro have been described (see Derijard et al., *Science* 267:682–685 (1995)). MKK3 appears to be specific for p38 (i.e., does not activate JNK or ERK), while MKK4 activates both p38 and JNK. MKK3 and MKK4 also stimulate the phosphorylation of p38 in certain cell lines after treatment with stimuli, such as ultraviolet radiation and NaCl. However, a stronger and more specific in vivo stimulator of p38 phosphorylation would have greater utility in therapeutic methods.

Accordingly, there is a need in the art for improved methods for modulating p38 activity and related enzymes or kinases in vivo, and for treating diseases associated with the p38 signal transduction pathway. The present invention fulfills these needs and further provides other related advantages.

SUMMARY OF THE INVENTION

Briefly stated, the present invention provides compositions and methods for modulating the activity of the mitogen-activated protein kinase (MAPK) p38. In one aspect, the present invention provides polypeptides comprising the amino acid sequence provided in SEQ ID NO:2 or a variant thereof that differs only in conservative substitutions and/or modifications at no more than 10% of the amino acid residues. Such variants include constitutively active polypeptides. In a related aspect, polypeptides comprising the amino acid sequence provided in SEQ ID NO:2 modified at no more than 10% of the amino acid residues, such that the polypeptides are rendered constitutively inactive, are provided.

In other aspects, isolated DNA molecules encoding polypeptides as described above, as well as recombinant expression vectors comprising such DNA molecules and host cells transformed or transfected with such expression vectors, are provided.

In further aspects, the present invention provides methods for phosphorylating p38, comprising contacting p38 with a polypeptide as described above, and for activating a member of the p38 cascade in an organism, comprising administering to an organism a polypeptide as described above. In a related aspect, the present invention provides methods for treating a patient afflicted with a disease associated with the p38 cascade, comprising administering to a patient a compound that promotes or inhibits the phosphorylation of p38 by MEK6.

Methods are also provided for screening for agents that inhibit or stimulate signal transduction via the p38 cascade. Such methods comprise: (a) contacting a candidate agent with a polypeptide as described above; and (b) subsequently measuring the ability of the polypeptide to activate p38. In yet another aspect, monoclonal antibodies that bind to a polypeptide as described above are provided.

Within further aspects, the present invention provides methods and kits for detecting MEK6 kinase activity in a sample. The methods comprise evaluating the ability of the sample to phosphorylate p38, thereby detecting MEK6 kinase activity in the sample. The kits for detecting MEK6 kinase activity in a sample comprise p38 in combination with a suitable buffer.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A and 1B present the nucleotide and primary amino acid sequence of MEK6, as deduced from the sequence of cDNA clones isolated from a human MOLT-4 cDNA library. For the amino acid sequence, standard one-letter codes are utilized.

FIG. 3A shows the level of autophosphorylation of the substrates GST (lane 1), GST-JNK2 (lane 2), GST-p38 (lane 3) and His-ERK1 [K52R] (lane 4) and the level of phosphorylation by GST-MEK6 of the substrates GST (lane 5), GST-JNK2 (lane 6), GST-p38 (lane 7) and His-ERK1 [K52R] (lane 8). FIG. 3B shows the results of a coupled kinase assay in which purified GST or GST-MEK6 was incubated with purified GST-JNK2, GST-p38 or GST in the presence of ATP. The proteins were isolated and washed, and then incubated with GST-cJun(1–79) (lanes 1–3) or GST-ATF2 (lanes 4–6) in the presence of [γ-$^{32}$P]ATP. Reactions were separated by SDS-PAGE and visualized by autoradiography. The position of protein molecular weight markers in kDa is shown on the left.

DETAILED DESCRIPTION OF THE INVENTION

Figure 2A:
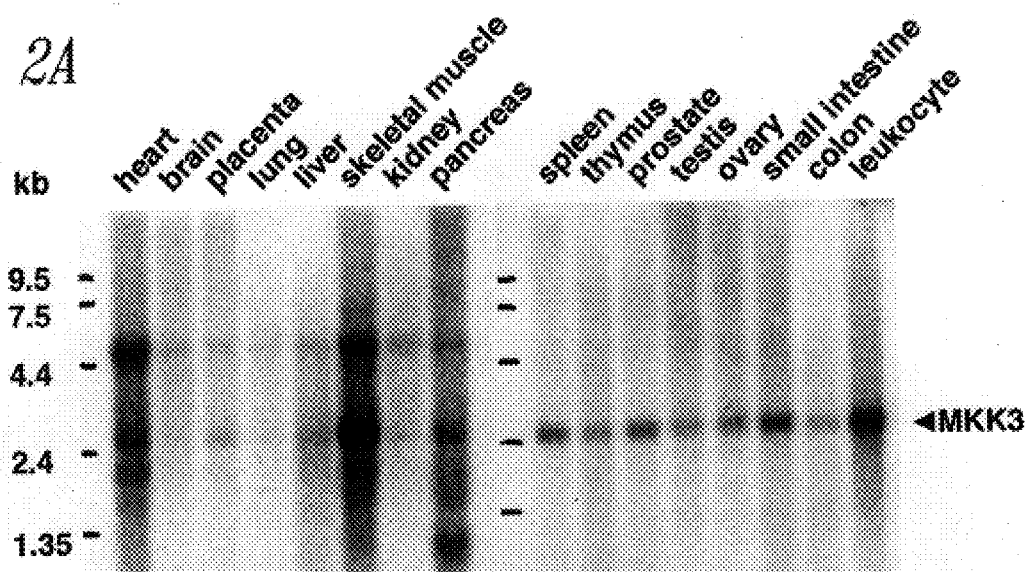
FIGS. 2A and 2B are autoradiograms that depict Northern blot analyses of the expression of human MKK3 (FIG. 2A) and human MEK6 (FIG. 2B) mRNA in selected adult human tissues. The position of RNA size markers in kb is shown on the left.

As noted above, the present invention is generally directed to compositions and methods for modulating (i.e., stimulating or inhibiting) the activity of the mitogen-activated protein kinase (MAPK) p38. Compositions that activate p38 generally stimulate p38 phosphorylation. Such compositions include polypeptides comprising the human mitogen-activated protein kinase kinase (MAPKK) MEK6, or a variant thereof that retains the ability to stimulate p38 phosphorylation. Alternatively, compositions that activate p38 may include nucleic acid sequences that encode MEK6 or a variant thereof. Polypeptide variants within the scope of the present invention differ from MEK6 in one or more conservative substitutions and/or modifications, at no more than 10% of the amino acid residues in the native polypeptide, such that the ability of the variant to stimulate p38 phosphorylation is not substantially diminished. Conservative substitutions may be made in non-critical and/or critical regions of the native protein. Variants may also, or alternatively, contain other conservative modifications, including the deletion or addition of amino acids that have minimal influence on the activity of the polypeptide. In particular, variants may contain additional amino acid sequences at the amino and/or carboxy termini. Such sequences may be used, for example, to facilitate purification or detection of the polypeptide.

Compositions that stimulate p38 phosphorylation (thereby activating p38) may also, or alternatively, include one or more agents that stimulate MEK6 kinase activity. Such agents include, but are not limited to, stress-inducing signals (e.g., UV, osmotic shock, DNA-damaging agents), anisomycin, LPS, and cytokines, and may be identified by combining a test compound with MEK6 in vitro and evaluating the effect of the test compound on the MEK6 kinase activity using, for example, a representative assay described herein.

Compositions that inactivate p38 generally inhibit p38 phosphorylation. Such compositions may include one or more agents that inhibit or block MEK6 activity, such as an antibody that neutralizes MEK6, a competing peptide that represents the substrate binding domain of MEK6 or the dual phosphorylation motif of the MEK6 substrate, an antisense polynucleotide or ribozyme that interferes with transcription and/or translation of MEK6, a molecule that inactivates MEK6 by binding to the kinase, a molecule that binds to the MEK6 substrate and prevents phosphorylation by MEK6 or a molecule that prevents transfer of phosphate groups from the kinase to the substrate. Alternatively, an agent that inactivates p38 may inhibit the kinase activity of phosphorylated p38.

Agents that inhibit MEK6 kinase activity may be identified by combining a test compound with MEK6 in vitro and evaluating the activity of the MEK6 using a MEK6 kinase assay. Agents that inhibit the activity of phosphorylated p38 may similarly be identified by combining a test compound with phosphorylated p38 and evaluating the effect of the test compound on the p38 kinase activity using, for example, one of the representative assays described herein.

DNA sequences encoding native MEK6 may be prepared by amplification from a suitable human cDNA library, using polymerase chain reaction (PCR) and methods well known to those of ordinary skill in the art. For example, an adapter-ligated cDNA library prepared from unstimulated Jurkat T cells may be screened using the 5' specific forward primer 5'-TTGTGCTCCCCTCCCCCATCAAA GGAA-3' (SEQ. ID NO. 3) and an adapter-specific primer. The resulting 1.6 kb cDNA has the sequence provided in SEQ ID NO: 1. The encoded MEK6 polypeptide, shown in SEQ ID NO:2, has a predicted size of 334 amino acids, with a calculated molecular weight of 37.5 kD. MEK6 is 88% identical to its closest homolog MKK3, and all relevant kinase subdomains are conserved. As shown in FIG. 1A and 1B the most divergent regions are the N-terminal region, with an additional 18 amino acids, and the C-terminal region.

Polypeptides of the present invention may be prepared by expression of recombinant DNA encoding the polypeptide in cultured host cells. Preferably, the host cells are bacteria, yeast, baculovirus-infected insect cells or mammalian cells. The recombinant DNA may be cloned into any expression vector suitable for use within the host cell, using techniques well known to those of ordinary skill in the art.

The DNA sequences expressed in this manner may encode MEK6, or may encode portions or other variants of MEK6. DNA molecules encoding variants of MEK6 may generally be prepared using standard mutagenesis techniques, such as oligonucleotide-directed site-specific mutagenesis, and sections of the DNA sequence may be removed to permit preparation of truncated polypeptides. As noted above, up to 10% of the amino acid residues may contain substitutions or other modifications, and any such changes preferably should not diminish the ability of the variant to stimulate p38 phosphorylation. In general, modifications may be more readily made in non-critical regions, which are regions of the native sequence that do not change the properties of MEK6. Non-critical regions may be identified by modifying the MEK6 sequence in a particular region and assaying the ability of the resulting variant in a kinase assay, using p38 as a substrate, as described herein.

As noted above, MEK6 may also be modified by the addition of sequences at the N- and/or C-terminus. For example, epitopes such as GST (glutathione-S-transferase), HA (hemagglutinin)-tag, FLAG and Histidine-tag may be added using techniques well known to those of ordinary skill in the art.

Modifications may also be made in critical regions of MEK6, provided that the resulting variant retains the ability to stimulate p38 phosphorylation. Critical regions include the ATP binding site $Lys^{69}$, and the dual phosphorylation motif ($Ser^{207}$, $Thr^{211}$). The effect of any modification on the ability of the variant to stimulate p38 phosphorylation may generally be evaluated using any assay for MEK6 kinase activity, such as the representative assays described herein.

Variants of MEK6 include constitutively active proteins. In general, activation of MEK6 in vivo requires stimulation by cytokines, UV, stress-inducing agents or osmotic shock. Constitutively active variants display the ability to stimulate p38 phosphorylation in the absence of such stimulation. Such variants may be identified using the representative in vivo assays for MEK6 kinase activity described herein. Preferred constitutively active variants include polypeptides in which the phospho-acceptor amino acids within the MEK6 dual phosphorylation motif ($Ser^{207}$ and $Thr^{211}$) are replaced with negatively charged amino acids such as glutamic acid or aspartic acid.

MEK6 may also be modified so as to render the protein constitutively inactive (i.e., unable to phosphorylate p38 even when stimulated as described above). For example, mutation of the conserved lysine in kinase subdomain I has been found to render MAPKKs inactive. Accordingly, a preferred constitutively inactive variant contains a modification of $Lys^{69}$ in kinase subdomain I of MEK6. Other such modifications may be identified using the representative assays described herein. Genes encoding proteins modified so as to be constitutively active or inactive may generally be used in replacement therapy for treatment of a variety of disorders, as discussed in more detail below.

Expressed polypeptides of this invention are generally isolated in substantially pure form. Preferably, the polypeptides are isolated to a purity of at least 80% by weight, more preferably to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

The present invention also provides methods for detecting the level of MEK6 in a sample, as well as for detecting MEK6 kinase activity in a sample. The level of MEK6, or nucleic acid encoding MEK6, may generally be determined using a reagent that binds to the MEK6 protein, DNA or RNA. To detect nucleic acid encoding MEK6, standard hybridization and/or PCR techniques may be employed using a nucleic acid probe or a PCR primer. Suitable probes and primers may be designed by those of ordinary skill in the art based on the MEK6 cDNA sequence provided in SEQ ID NO: 1. To detect MEK6 protein, the reagent is typically an antibody, which may be prepared as described below. There are a variety of assay formats known to those of ordinary skill in the art for using an antibody to detect a polypeptide in a sample. See, e.g., Harlow and Lane, *Antibodies: A Laboratory Manual*, Cold Spring Harbor Laboratory, 1988. For example, the antibody may be immobilized on a solid support such that it can bind to and remove the polypeptide from the sample. The bound polypeptide may then be detected using a second antibody that binds to the antibody/peptide complex and contains a detectable reporter group. Alternatively, a competitive assay may be utilized, in which polypeptide that binds to the immobilized antibody is labeled with a reporter group and allowed to bind to the immobilized antibody after incubation of the antibody with the sample. The extent to which components of the sample inhibit the binding of the labeled polypeptide to the antibody is indicative of the level of polypeptide within the sample. Suitable reporter groups for use in these methods include, but are not limited to, enzymes (e.g., horseradish peroxidase), substrates, cofactors, inhibitors, dyes, radionuclides, luminescent groups, fluorescent groups and biotin.

MEK6 kinase assays, for use in evaluating the polypeptide variants and other agents discussed above, include any assays that evaluate a compound's ability to phosphorylate p38, thereby rendering the p38 active (i.e., capable of phosphorylating in vivo substrates such as ATF2). p38 for use in such methods may be endogenous, purified or recombinant, and may be prepared using any of a variety of techniques that will be apparent to those of ordinary skill in the art. For example, cDNA encoding p38 may be cloned by PCR amplification from a suitable human cDNA library, using primers based on the published sequence (Han et al., Science 265:808–811 (1994); Lee et al., Nature 372:739–746 (1994)). p38 cDNA may then be cloned into a bacterial expression vector and the protein produced in bacteria, such as *E. coli*, using standard techniques. The bacterial expression vector may, but need not, include DNA encoding an epitope such as glutathione-S transferase protein (GST) such that the recombinant protein contains the epitope at the N- or C-terminus.

A MEK6 kinase assay may be performed substantially as described in Derijard et al., *Cell* 76:1025–1037 (1994) and Lin et al., *Science* 268:286–290 (1995), with minor modifications. Briefly, a polypeptide variant of MEK6 may be incubated with p38 and [γ-$^{32}$P]ATP in a suitable buffer (such as 20 mM HEPES (pH 7.6), 5 mM $MnCl_2$, 10 mM $MgCl_2$, 1 mM dithiothreitol) for 30 minutes at 30° C. In general, approximately 0.5 μg of the variant and 1 μg recombinant p38, with 50 nM [γ-$^{32}$P]ATP, is sufficient. Proteins may then be separated by SDS-PAGE on 10% gels and subjected to autoradiography. Incorporation of [$^{32}$P]phosphate into p38 may be quantitated using techniques well known to those of ordinary skill in the art, such as with a phosphorimager. To evaluate the substrate specificity of polypeptide variants, a kinase assay may generally be performed as described above except that other MAPK substrates (i.e., JNK2 and/or ERK) are substituted for the p38.

To determine whether p38 phosphorylation results in activation, a coupled in vitro kinase assay may be performed using a substrate for p38, such as ATF2, with or without an epitope tag. ATF2 for use in such an assay may be prepared as described in Gupta et al., *Science* 267:389–393 (1995). Briefly, following phosphorylation of p38 as described above, isolation of the protein by binding to GSH-sepharose and washing with 20 mM HEPES (pH 7.6), 20 mM MgCl$_2$, the p38 (0.1–10 µg) may be incubated with ATF2 (0.1–10 µg) and [γ-$^{32}$P]ATP (10–500 nM) in a buffer containing 20 mM HEPES (pH 7.6), 20 mM MgCl$_2$. It should be noted that alternative buffer may be used and that buffer composition can vary without significant effects on kinase activity. Reactions may be separated by SDS-PAGE, visualized by autoradiography and quantitated using any of a variety of known techniques. Activated p38 will be capable of phosphorylating ATF2 at a level of at least 5% above background using this assay.

To evaluate the effect of an antibody or other candidate modulating agent on MEK6 activity, a kinase assay may be performed as described above, except that MEK6 (rather than a variant thereof) is generally employed and the candidate modulating agent is added to the incubation mixture. The candidate agent may be preincubated with MEK6 kinase before addition of ATP and substrate. Alternatively, the substrate may be preincubated with the candidate agent before the addition of kinase. Further variations include adding the candidate agent to a mixture of kinase and ATP before the addition of substrate, or a mixture of substrate and ATP before the addition of MEK6 kinase, respectively. All these assays can further be modified by removing the candidate agent after the initial preincubation step. In general, a suitable amount of antibody or other candidate agent for use in such an assay ranges from about 0.1 µM to about 10 µM. The effect of the agent on MEK6 kinase activity may then be evaluated by quantitating the incorporation of [$^{32}$P]phosphate into p38, as described above, and comparing the level of incorporation with that achieved using MEK6 without the addition of the candidate agent.

MEK6 activity may also be measured in whole cells transfected with a reporter gene whose expression is dependent upon the activation of ATF2. For example, cells may be transfected with an ATF2-dependent promoter linked to a reporter gene such as luciferase. In such a system, expression of the luciferase gene (which may be readily detected using methods well known to those of ordinary skill in the art) depends upon activation of ATF2 by p38, which may be achieved by the stimulation of MEK6 with an activator or by cotransfection with an expression vector that produces a constitutively active variant of MEK6. Candidate modulating agents may be added to the system, as described below, to evaluate their effect on MEK6 activity.

Alternatively, a whole cell system may employ only the transactivation domain of ATF2 fused to a suitable DNA binding domain, such as GHF-1 or GAL4. The reporter system may then comprise the GH-luciferase or GAL4-luciferase plasmid. Candidate MEK6 modulating agents may then be added to the system to evaluate their effect on ATF2-specific gene activation.

In other aspects of the subject invention, methods for using the above polypeptides to phosphorylate and activate p38, or peptide derivatives thereof, are provided. p38 substrate for use in such methods may be prepared as described above. In one embodiment, p38 may be phosphorylated in vitro by incubating p38 with MEK6, or a variant thereof, and ATP in a suitable buffer as described above for 30 minutes at 30° C. In general, the amounts of the reaction components may range from about 0.1 µg to about 10 µg of MEK6 or a variant thereof, from about 0.1 µg to about 10 µg of recombinant p38, and from about 10 nM to about 500 nM of ATP. Phosphorylated proteins may then be purified by binding to GSH-sepharose and washing. The extent of p38 phosphorylation may generally be monitored by adding [γ-$^{32}$P]ATP to a test aliquot, and evaluating the level of p38 phosphorylation as described above. The activity of the phosphorylated p38 may be evaluated using a coupled in vitro kinase assay, as described above.

Once activated in vitro, p38 may be used, for example, to identify agents that inhibit the kinase activity of p38. Such inhibitory agents, which may be antibodies or drugs, may be identified using the coupled assay described above. Briefly, a candidate agent may be included in the mixture of p38 and ATF2, with or without pre-incubation with one or more components of the mixture, as described above. In general, a suitable amount of antibody or other agent for use in such an assay ranges from about 0.1 µM to about 10 µM. The effect of the agent on p38 kinase activity may then be evaluated by quantitating the incorporation of [$^{32}$P] phosphate into ATF2, as described above, and comparing the level of incorporation with that achieved using activated p38 without the addition of a candidate agent.

The above polypeptides and/or modulating agents may also be used to phosphorylate, and thereby activate, p38 in a patient. As used herein, a "patient" may be any mammal, including a human, and may be afflicted with a disease associated with the p38 cascade or may be free of detectable disease. Accordingly, the treatment may be of an existing disease or may be prophylactic. Diseases associated with the p38 cascade include any disorder which is etiologically linked to MEK6 kinase activity, including immune-related diseases (e.g., inflammatory diseases, autoimmune diseases, malignant cytokine production or endotoxic shock), cell growth-related diseases (e.g., cancer, metabolic diseases, abnormal cell growth and proliferation or cell cycle abnormalities) and cell regeneration-related diseases (e.g., cancer, degenerative diseases, trauma, environmental stress by heat, UV or chemicals or abnormalities in development and differentiation).

For administration to a patient, one or more polypeptides and/or modulating agents are generally formulated as a pharmaceutical composition, formulated as a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of this invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases.

Alternatively, a pharmaceutical composition may contain DNA encoding a polypeptide as described above, such that MEK6 or a variant thereof is generated in situ, in combination with a physiologically acceptable carrier. In such pharmaceutical compositions, the DNA may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary DNA sequences for expression in the patient (such as a suitable promoter and terminating signal). The DNA may also be "naked," as described, for example, in Ulmer et al., *Science* 259:1745–1749 (1993).

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for MEK6 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci. 6:77, 1981). In addition to mammalian cells, liposomes have been used for delivery of polynucleotides in plant, yeast and bacterial sells. In order for a liposome to be an efficient gene transfer vehicle, the following characteristics should be present. (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques 6:882, 1988).

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration and polypeptide, modulating agent or nucleic acid doses will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount of polypeptide or DNA that is sufficient to show improvement in the symptoms of a patient afflicted with a disease associated with the p38 cascade. Such improvement may be detected based on a determination of relevant cytokine levels (e.g., IL-2, IL-8), by monitoring inflammatory responses (e.g., edema, transplant rejection, hypersensitivity) or through an improvement in clinical symptoms associated with the disease. In general, the amount of polypeptide present in a dose, or produced in situ by DNA present in a dose, ranges from about 1 μg to about 250 μg per kg of host, typically from about 1 μg to about 60 μg. Suitable dose sizes will vary with the size of the patient, but will typically range from about 10 mL to about 500 mL for 10–60 kg animal.

The MEK6 protein kinase described herein is also useful in a screening method for identifying compounds or compositions which affect the activity of the kinase. Thus, in another embodiment, the invention provides methods for identifying a composition which affects MEK6 activity comprising incubating the components, which include the composition to be tested and the kinase or a polynucleotide encoding the kinase, under conditions sufficient to allow the components to interact, then subsequently measuring the effect the composition has on kinase activity or on a polynucleotide encoding the kinase. The observed effect on the kinase may be either inhibitory or stimulatory. For example, the increase or decrease of the kinase activity can be measured by adding a radioactive compound to the mixture of components such as $^{32}$P-ATP, and observing radioactive incorporation into p38 or other suitable substrates for MEK6, to determine whether the compound inhibits or stimulates kinase activity. A polynucleotide encoding the kinase may be inserted into an expression vector and the effect of a composition on transcription of the kinase can be measured, for example, by Northern blot analysis.

In another embodiment, the invention provides a method of treating immunological-related cell proliferative diseases such as osteoarthritis, ischemia, reperfusion injury, trauma, certain cancers and viral disorders, and autoimmune diseases such as rheumatoid arthritis, multiple sclerosis, psoriasis, inflammatory bowel disease, and other acute phase responses. Essentially, any disorder which is etiologically linked to MEK6 kinase activity would be considered susceptible to treatment.

Treatment includes administration of a composition or compound which modulates MEK6 kinase activity. Such modulation includes the suppression of expression of MEK6 when it is over expressed, or augmentation of MEK6 expression when it is under expressed. Modulation may also include suppression of phosphorylation of p38 or related kinases.

As noted above, the present invention also encompasses antibodies, which may be polyclonal or monoclonal, specific for MEK6 and/or one or more variants thereof. Preferred antibodies are those antibodies that inhibit or block MEK6 activity in vivo and within a MEK6 kinase assay as described above. Antibodies may be prepared by any of a variety of techniques known to those of ordinary skill in the art (see, e.g., Harlow and Lane, *Antibodies. A Laboratory Manual*, Cold Spring Harbor Laboratory, 1988). In one such technique, an immunogen comprising the polypeptide is initially injected into a suitable animal (e.g., mice, rats, rabbits, sheep and goats), preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for MEK6 or a variant thereof may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Antibodies and other agents having a desired effect on MEK6 activity, as described above, may be administered to a patient (either prophylactically or for treatment of an existing disease) to modulate the activation of p38 in vivo. For example, an agent that decreases MEK6 activity in vivo may be administered to prevent or treat inflammation, autoimmune diseases, cancer or degenerative diseases. In general, for administration to a patient, an antibody or other agent is formulated as a pharmaceutical composition which additionally comprises a physiologically acceptable carrier. Any suitable carrier known to those of ordinary skill in the art may be employed in the pharmaceutical compositions of this invention, including the representative carriers described above.

A pharmaceutical composition may also, or alternatively, contain DNA encoding an antibody or other agent as described above, such that the active agent is generated in situ. In such pharmaceutical compositions, the DNA may be introduced using any of a variety of delivery systems known to those of ordinary skill in the art, such as those described above. For administration of such agents, routes, frequency and doses will vary from patient to patient. In general, however, the pharmaceutical compositions may be administered as described above. A suitable dose of such an agent is an amount sufficient to show benefit in the patient based on the criteria noted above.

In a related aspect of the present invention, kits for detecting MEK6 and MEK6 kinase activity are provided. Such kits may be designed for detecting the level of MEK6 or nucleic acid encoding MEK6, or may detect phosphorylation of p38 in a direct kinase assay or a coupled kinase assay, in which both the level of phosphorylation and the kinase activity of p38 may be determined. MEK6 and MEK6 kinase activity may be detected in any of a variety of samples, such as eukaryotic cells, bacteria, viruses, extracts prepared from such organisms and fluids found within living organisms. In general, the kits of the present invention comprise one or more containers enclosing elements, such as reagents or buffers, to be used in the assay.

A kit for detecting the level of MEK6, or nucleic acid encoding MEK6, typically contains a reagent that binds to the MEK6 protein, DNA or RNA. To detect nucleic acid encoding MEK6, the reagent may be a nucleic acid probe or a PCR primer. To detect MEK6 protein, the reagent is typically an antibody. The kit also contains a reporter group suitable for direct or indirect detection of the reagent (i.e., the reporter group may be covalently bound to the reagent or may be bound to a second molecule, such as Protein A, Protein G, immunoglobulin or lectin, which is itself capable of binding to the reagent). Suitable reporter groups include, but are not limited to, enzymes (e.g. horseradish peroxidase), substrates, cofactors, inhibitors, dyes, radionuclides, luminescent groups, fluorescent groups and biotin. Such reporter groups may be used to directly or indirectly detect binding of the reagent to a sample component using standard methods known to those of ordinary skill in the art.

A kit for detecting MEK6 kinase activity based on measuring the phosphorylation of p38 generally comprises p38 in combination with a suitable buffer. A kit for detecting MEK6 kinase activity based on detecting p38 activity generally comprises p38 in combination with a suitable p38 substrate, such as ATF2. Optionally, the kit may additionally comprise a suitable buffer and/or material for purification of p38 after activation and before combination with ATF2. Such kits may be employed in direct or coupled MEK6 kinase assays, which may be performed as described above.

In yet another aspect, MEK6 or a variant thereof may be used to identify one or more native upstream kinases (i.e., kinases that phosphorylate and activate MEK6 in vivo). MEK6 may be used in a yeast two-hybrid system to identify proteins that interact with MEK6. Alternatively, an expression library may be sequenced for cDNAs that phosphorylate MEK6.

The following Examples are offered by way of illustration and not by way of limitation.

EXAMPLES

Example 1

Cloning and Sequencing cDNA Encoding MEK6

This Example illustrates the cloning of a cDNA molecule encoding the human MAPKK MEK6.

The Expressed Sequence Tags (EST) subdivision of the National Center for Biotechnology Information (NCBI) Genbank databank was searched with the tblastn program and the human MKK3 amino acid sequence (Derijard et al., *Science* 267:682–685 (1995)) as query using the BLAST e-mail server. The 223 bp EST sequence F00521 displayed the highest similarity score. A reverse PCR primer (5'-CACATCTTCACTTGACCGAGAGCA-3') (SEQ. ID NO. 4) directed against this sequence was designed with the help of the program Oligo V.4.0 (National Biosciences, Inc., Plymouth, Minn.).

PolyA+RNA was prepared from unstimulated Jurkat T cells using the Micro-Fast Track Kit (Invitrogen, San Diego, Calif.). One μg of this RNA was used to generate an adaptor-ligated cDNA library that can be used for 5' and 3' RACE (Marathon cDNA Amplification Kit, Clontech Laboratories, Palo Alto, Calif.). The adaptor specific primer from the kit and the gene specific reverse primer were used to PCR-amplify the 5' portion of MEK6. PCR amplification was performed with a combination of Taq and Pwo polymerases (Expand Long Template PCR System, Boehringer-Mannheim Corp., Indianapolis, Ind.) in the presence of TaqStart antibody (Clontech Laboratories, Palo Alto, Calif.). This mixture is designed to produce high yield of long PCR fragments and proof-reading function. All PCR amplifications were carried out in 0.2 ml Perkin-Elmer thin-wall MicroAmp tubes and a Perkin-Elmer model 2400 or 9600 thermocycler. The resulting 0.8 kb PCR fragment was ligated into pGEM-T (Promega, Madison, Wis.) and sequenced (dye terminator cycle sequencing) with an ABI 373 Automated Sequencer (Applied Biosystems, Inc., Foster City, Calif.).

The sequence information from the 5' end of the partial MEK6 cDNA was used to design a forward PCR primer (5'-TTGTGCTCCCCTCCCCCATCAAAGG AA-3') (SEQ. ID NO. 3) for 3' RACE. The gene specific forward primer and the adaptor specific primer were used to PCR-amplify the complete MEK6 cDNA from an adaptor-ligated MOLT-4 cDNA library. This library was generated using one μg MOLT-4 polyA+RNA (Clontech Laboratories, Palo Alto, Calif.) and the Marathon cDNA Amplification Kit (Clontech Laboratories, Palo Alto, Calif.). The 1.6 kb PCR fragment was ligated into pGEM-T (Promega, Madison, Wis.) and three clones were sequenced several times on both strands with an ABI 373 Automated Sequencer. A BLAST search of the NCBI Genbank database for related cDNAs revealed no similar sequences. The 1.6 kb cDNA encodes a potential protein of 334 amino acids with a calculated molecular weight of 37.5 kDalton.

The Bestfit program (Wisconsin Genetics Computer Group, Madison, Wis.) was used for calculating the amino acid identities between MEK6 and MKK3, its closest homolog. The MacVector program (Kodak-IBI, Rochester, N.Y.) was used for aligning the amino acids of MKK3 and MEK6. MEK6 has 88% amino acid identity with MKK3, and all relevant kinase subdomains, the ATP acceptor site and phosphorylation sites are conserved. The most divergent regions are the N-terminal region, with an additional 18 amino acids, and the C-terminal region (FIGS. 1A and 1B).

Example 2

In Vivo Expression of MEK6

This Example illustrates the expression of MEK6, as compared to MKK3, in various human tissues.

Northern blots were performed using 2 μg of polyA+RNA isolated from 16 different adult human tissues, fractionated by denaturing formaldehyde 1.2% agarose gel electrophoresis, and transferred onto a charge-modified nylon membrane (Clontech Laboratories, Palo Alto, Calif.). The blots were hybridized to a MKK3 probe (700 bp MKK3 cDNA fragment) or MEK6 probe (870 bp MEK6 cDNA fragment) using ExpressHyb (Clontech Laboratories, Palo Alto, Calif.) according to the manufacturer's instructions. Both probes were prepared by labeling the cDNA with [α-$^{32}$P]dCTP (NEN, Boston, Mass.) by random priming (Stratagene, La Jolla, Calif.). For control purposes, the blots were also hybridized to a radiolabeled β-actin probe.

Figure 2B:
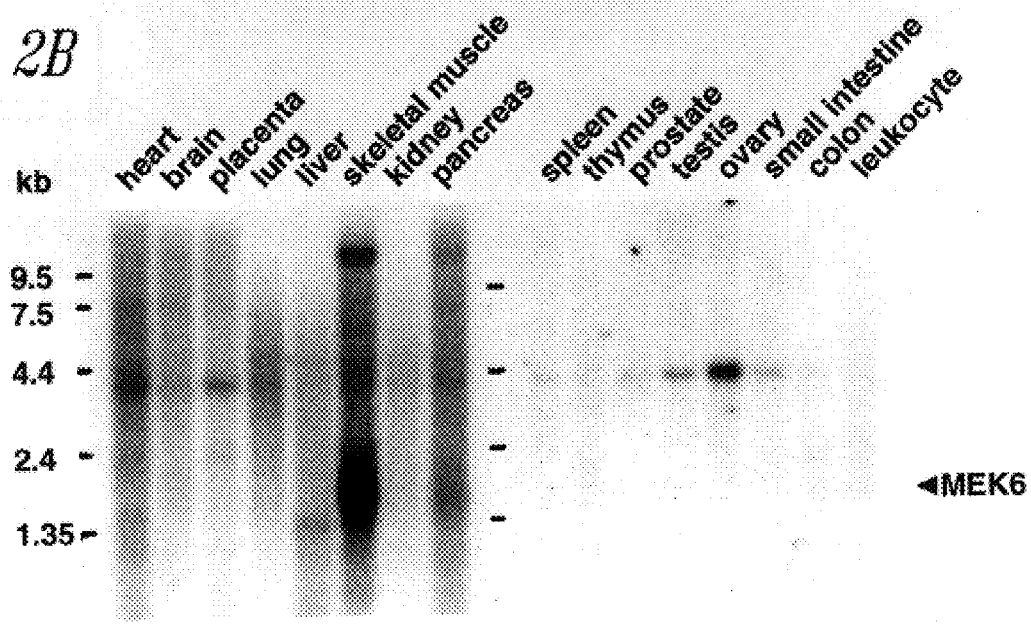

The results, shown in FIGS. 2A and 2B, demonstrate that MKK3 is widely expressed in many adult human tissues with highest levels in skeletal muscle and leukocytes (FIG. 2A). In contrast, MEK6 is predominantly expressed in skeletal muscle and at lower levels in heart and pancreas (FIG. 2B). No MEK6 was detected in spleen, thymus, prostate, ovary, small intestine, colon or leukocyte. All 16 tissues analyzed expressed equal amounts of β-actin mRNA. Some of the tissues expressed an MEK6-related mRNA of about 4.2 kb, which was not observed when MEK6 specific probe directed against the 3' of MEK6 cDNA was used.

Example 3

Substrate Specificity of MEK6

This Example illustrates the kinase activity and substrate specificity of MEK6, as compared to MKK3, in in vitro and in vivo assays.

cDNAs encoding MEK6 and MKK3 were subcloned into a bacterial GST-fusion protein expression vector. GST-MEK6 was constructed by ligating a 1.3 kb DNA fragment encoding amino acid 1 through the stop codon of MEK6 with a serine to alanine substitution of amino acid 2 into pGEX-KG (Guan and Dixon, *Ann. Biochem.* 192:262–267 (1991)). Similarly, GST-MKK3, GST-p38 and GST-JNK2 were constructed by ligating the respective cDNA fragments encoding amino acid 1 through the stop codon into pGEX-KG. Human p38 cDNA (Genbank accession number U10871) was cloned by PCR amplification of a Jurkat cDNA library with primers against the 5' end (5'-CCAACCATGGCTCAGGAGAG-3') (SEQ. ID NO. 5) and 3' end (5'-CGGTACCTTCAGGACTCCATCT-3') (SEQ. ID NO. 6) of the published human p38 sequence. Each strand of the PCR fragment was sequenced several times with an ABI 373 Automated Sequencer. His-ERK1 [K52R] was prepared as described previously (Robbins et al., *J Biol. Chem.* 268:5097–5106 (1993)).

We investigated the substrate specificity of MEK6 in an in vitro kinase assay with bacterially expressed MAPK substrates (GST-JNK2, GST-p38 and His-ERK1[K52R]). The assays were performed as previously described (Derijard et al., *Cell* 76:1025–1037 (1994); Lin et al., *Science* 268:286–290 (1995)) with minor modifications. 0.5 μg recombinant kinase and 1 μg recombinant substrate were used, and the concentration of [γ-$^{32}$P]ATP was 50 nM. Phosphorylated proteins were separated by SDS-PAGE on 10% gels and then subjected to autoradiography. Incorporation of [$^{32}$P]phosphate was quantitated with a phosphorimager and ImageQuant software (Molecular Dynamics, Inc., Sunnyvale, Calif.).

Figure 3A:
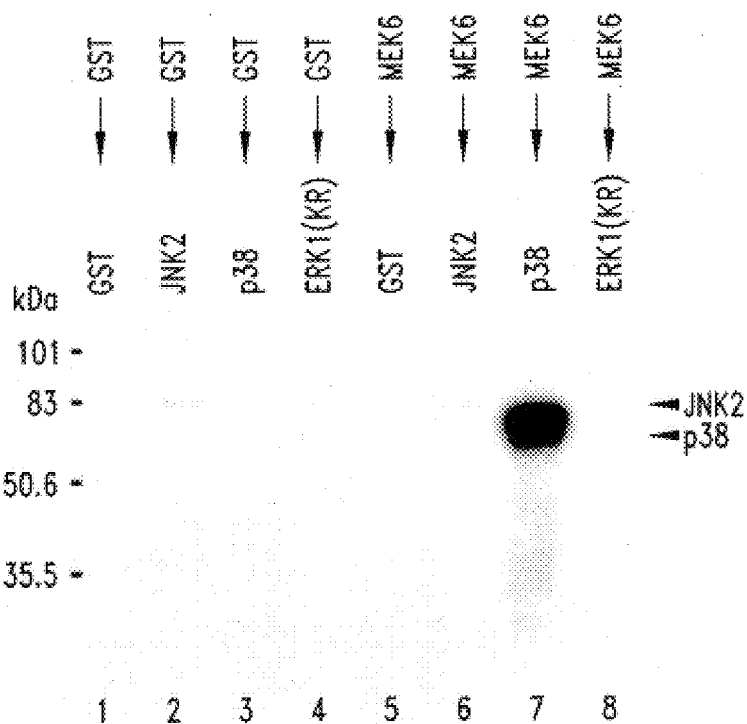
FIGS. 3A and 3B are autoradiograms that present the results of kinase assays evaluating the substrate specificity of MEK6.

FIG. 3A shows the level of autophosphorylation of the substrates GST (lane 1), GST-JNK2 (lane 2), GST-p38 (lane 3) and His-ERK1[K52R] (lane 4) and the level of phosphorylation by GST-MEK6 of the substrates GST (lane 5), GST-JNK2 (lane 6), GST-p38 (lane 7) and His-ERK1 [K52R] (lane 8). In each case, 1 μg of the purified recombinant substrate was used. Autophosphorylation of MEK6 was very low compared to MKK3. JNK2 autophosphorylated, whereas p38 and ERK1(K52R) did not. MEK6 efficiently phosphorylated p38 but none of the other substrates (FIG. 3A, compare lanes 1 to 4 with 5 to 8), although in parallel experiments the phosphorylation of JNK by JNKK has been observed (data not shown). This indicates that MEK6 has a substrate selectivity for the p38 subgroup of MAPKs.

Figure 3B:
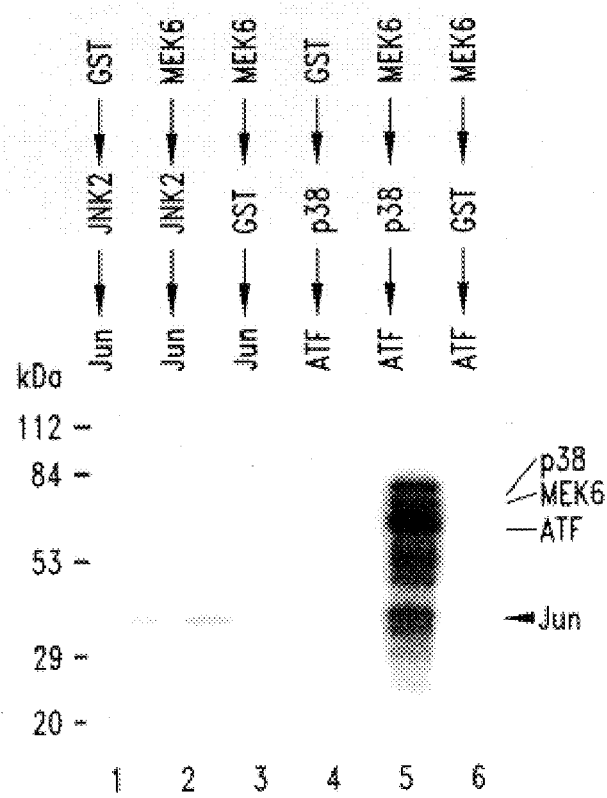

To determine whether phosphorylation of p38 is an activating event we analyzed the phosphorylation of recombinant ATF2 (a substrate for p38) in a coupled in vitro kinase assay. GST-ATF2 was prepared as previously described (Gupta et al., *Science* 267:389–393 (1995). FIG. 3B shows the results of a coupled kinase assay in which purified GST or GST-MEK6 (0.1–10 μg) was incubated with purified GST-JNK2 (lanes 1 and 2), GST-p38 (lanes 4 and 5) or GST (lanes 3 and 6) (0.1–10 μg) in the presence of JNKK buffer (Lin et al., *Science* 268:286–290 (1995)) and 100 μM ATP. The proteins were isolated by binding to GSH-sepharose and after washing with 20 mM HEPES (pH 7.6), 20 mM MgCl$_2$, incubated with GST-cJun(1–79) (lanes 1–3) or GST-ATF2 (lanes 4–6) (0.1–10 μg) in the presence of JNK buffer with 20 mM HEPES (pH 7.6), 20 mM MgCl$_2$, and [γ-$^{32}$P]ATP (10–500 nM). Reactions were separated by SDS-PAGE and visualized by autoradiography.

MEK6 did not cause increased phosphorylation of Jun (GST-Jun(1–79), prepared as described in Hibi et al., *Genes and Development* 7:2135–2148 (1993)) either directly or in combination with JNK2 (FIG. 3B, lanes 1 to 3). ATF2, however, was strongly phosphorylated by p38 that has been activated by MEK6 (FIG. 3B, lane 5). ATF2 was not directly phosphorylated by MEK6. These data establish that MEK6 is a functional MAPKK in vitro and that MEK6 specifically phosphorylates p38, resulting in its activation.

Next, we examined whether MEK6 can activate p38 in vivo. An expression vector encoding epitope-tagged MEK6 (3×HA-MEK6-SRα3) was constructed by replacing serine in position 2 of MEK6 with alanine, adding sequence encoding three copies of a 10 amino acid hemagglutinin (HA) epitope to the N-terminus of MEK6 and ligating the resulting cDNA into SRα3. HeLa cells, cultured in Dulbecco's modified Eagle medium supplemented with 10% fetal calf serum, 500 mg/l L-glutamine, and antibiotics, were transiently transfected with 333 HA-MEK6 using calcium phosphate-mediated DNA precipitation (Graham and van der Eb, *Virology* 52:456–467 (1973)). Twenty-four hours later cells were stimulated with anisomycin (50 ng/mL) or UV (254 nm; 120 J/m$^2$) for 0–120 minutes. Cell lysates were prepared by solubilization in lysis buffer as described (Derijard et al., *Cell* 76:1025–1037 (1994)), and protein concentration of lysates was determined by Bradford assay (Bradford, *Ann. Biochem.* 72:248–254 (1976)).

In an initial experiment we investigated the time course of MEK6 activation by anisomycin and UV treatment of transfected cells. Cell lysates were used in an immune complex kinase assay with GST-p38 substrate, performed as described above except that 30 μg cell lysate was immunoprecipitated for 2 hours with the anti-HA antibody 12CA5 (Boehringer-Mannheim Corp., Indianapolis, Ind.) and then incubated with 1 μg of recombinant substrate. Reactions were separated by SDS-PAGE and quantitated with a phosphorimager and ImageQuant software. The relative level of MEK6 activity in untreated cells was arbitrarily assigned 1. The presence of equal amounts of MEK6 in all kinase reactions was confirmed by Western blot analysis (data not shown).

Figure 4:
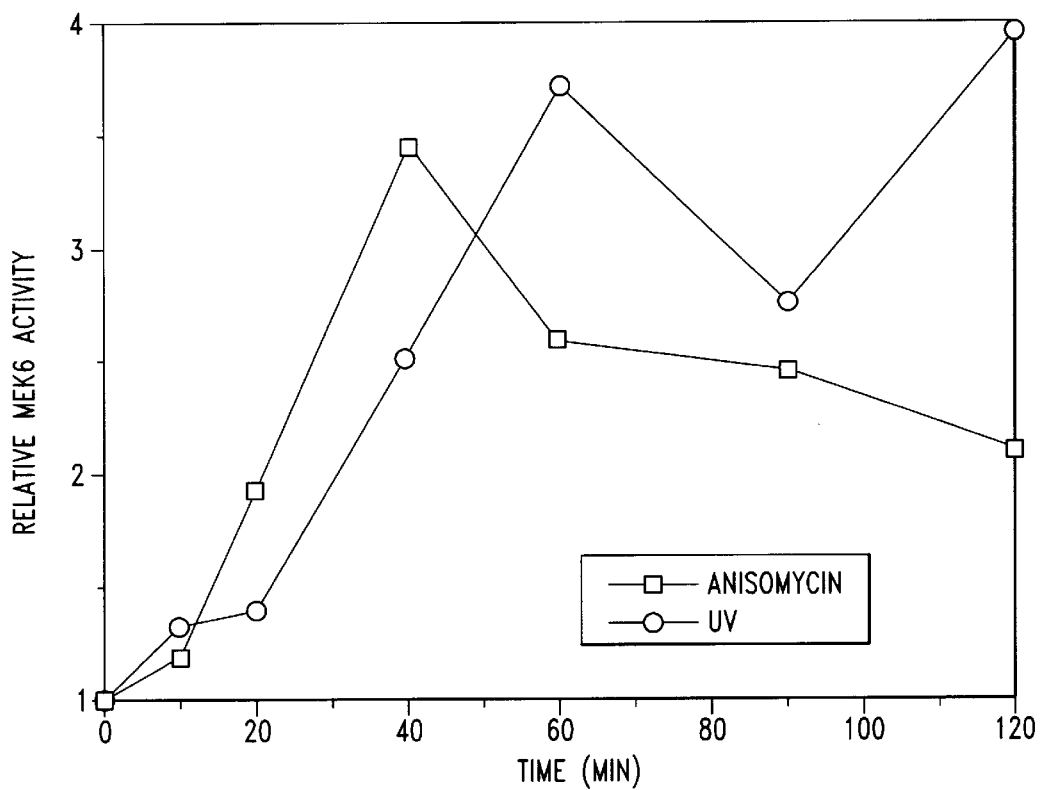
FIG. 4 is a graph depicting the relative levels of MEK6 kinase activity in HeLa cells transiently transfected with epitope-tagged MEK6 and treated with anisomycin (50 ng/ml) or UV (254 nm; 120 J/m$^2$) for the times indicated. The relative level of MEK6 activity in untreated cells was arbitrarily assigned to be 1.
Figure 5:
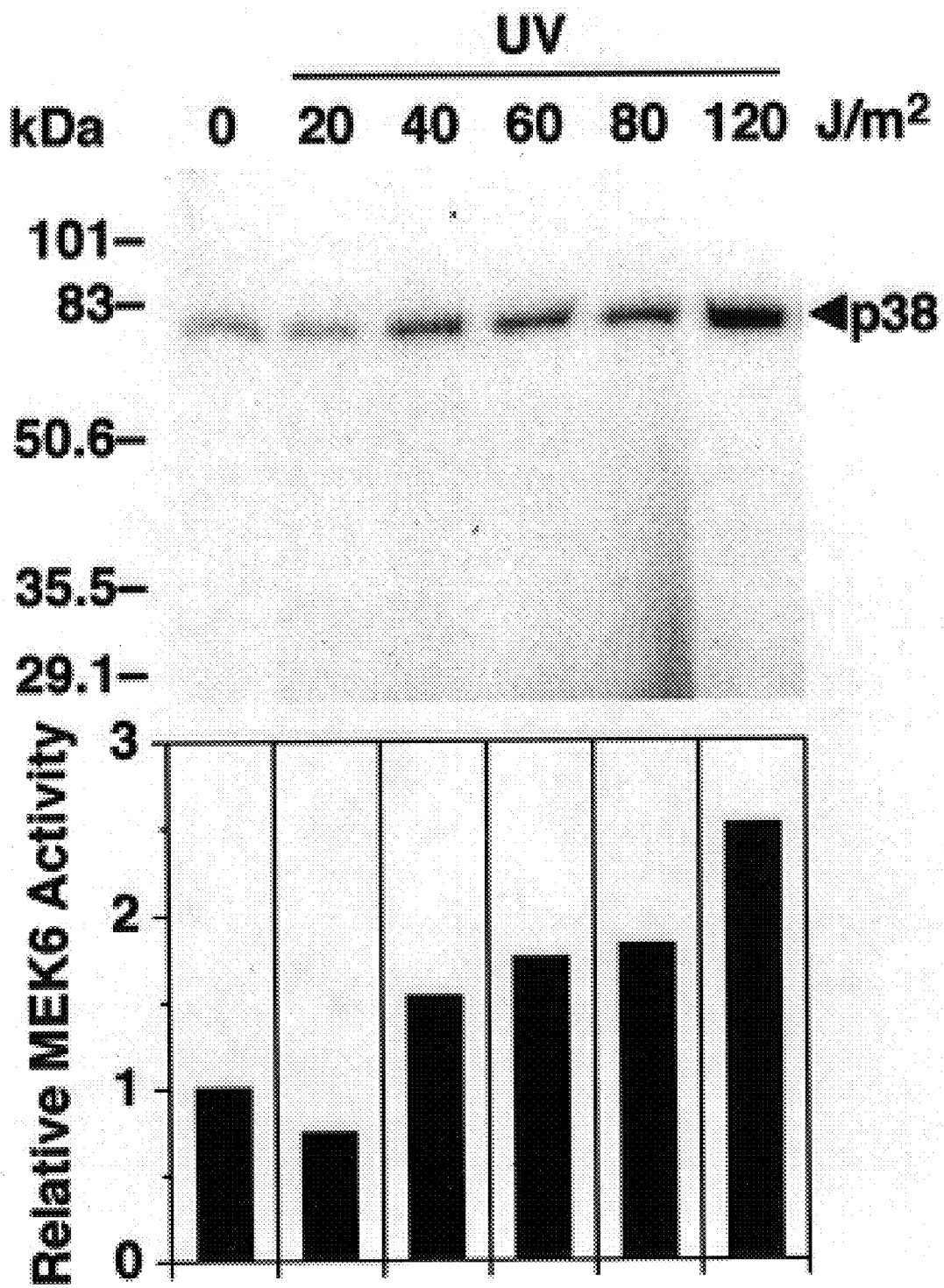
FIG. 5 is an autoradiogram and graph presenting the relative levels of MEK6 kinase activity in HeLa cells transiently transfected with epitope-tagged MEK6 and activated for 40 min with 20 to 120 J/m$^2$ UV (254 nm) as indicated. Reactions were separated by SDS-PAGE and visualized by autoradiography. The position of protein molecular weight markers in kDa is shown on the left. MEK6 activity was quantitated with a phosphorimager and ImageQuant software and is shown in the bar graph.

MEK6 activation by anisomycin as measured by its ability to phosphorylate p38, was observed as early as 10 min after treatment (FIG. 4). The activation was transient and peaked at 40 min after treatment. In contrast, activation by UV was delayed by about 10 to 15 min and declined only slowly after a peak at 60 min (FIG. 4). Analysis of the UV dose response of MEK6 in HeLa cells revealed that doses up to 120 J/m$^2$ yielded increasing activity of MEK6 (FIG. 5).

Figure 6:
FIG. 6 is an autoradiogram depicting the relative levels of MEK6 kinase activity in HeLa cells transiently transfected with epitope-tagged MEK6 (lanes 1–8) or the empty expression vector SRα3 (lanes 9–16) and treated for 45 min with Anisomycin (An., 50 ng/ml) or left untreated (ctrl) as indicated. The position of protein molecular weight markers in kDa is illustrated on the left. The position of p38, ATF2 and an unknown protein (*) is indicated on the right.

To determine whether the increase in p38 phosphorylation by activated MEK6 augments p38 kinase activity a coupled immune complex kinase assay was performed. Epitope-tagged MEK6 was isolated from anisomycin-treated HeLa cells (45 minutes; 50 ng/mL) and subjected to two subsequent kinase reactions as described above using recombinant p38, ATF2 and GST alone. In support of our in vitro results, anisomycin treatment caused increased phosphorylation of ATF2 only when MEK6 and p38 were present (FIG. 6, compare lanes 5, 6 with 7, 8). Similar results have been found with MEK6 activated by UV treatment of cells (data not shown). No inducible phosphorylation of p38 or ATF2 was observed in HeLa cells transfected with the empty expression vector SRα3 (FIG. 6, compare lanes 5, with 13, 14). This clearly indicates that the inducible phosphorylation of ATF2 depends on a kinase cascade comprised of MEK6 and p38. Interestingly, p38 also phosphorylated weakly a protein with a mobility slightly faster than ATF2 (indicated by * in FIG. 6). This phosphorylation event was slightly augmented by anisomycin in the presence of MEK6 (FIG. 6, compare lanes 3 and 4 with lanes 11 and 12). This protein was not observed in in vitro kinase assays, and therefore is most likely a contamination of the immunoprecipitation.

Example 4

Activation of MEK6 by Stress-Inducing Agents

This Example illustrates the response of MEK6 to a variety of stimulators of the MAPK pathway.

Figure 7A:
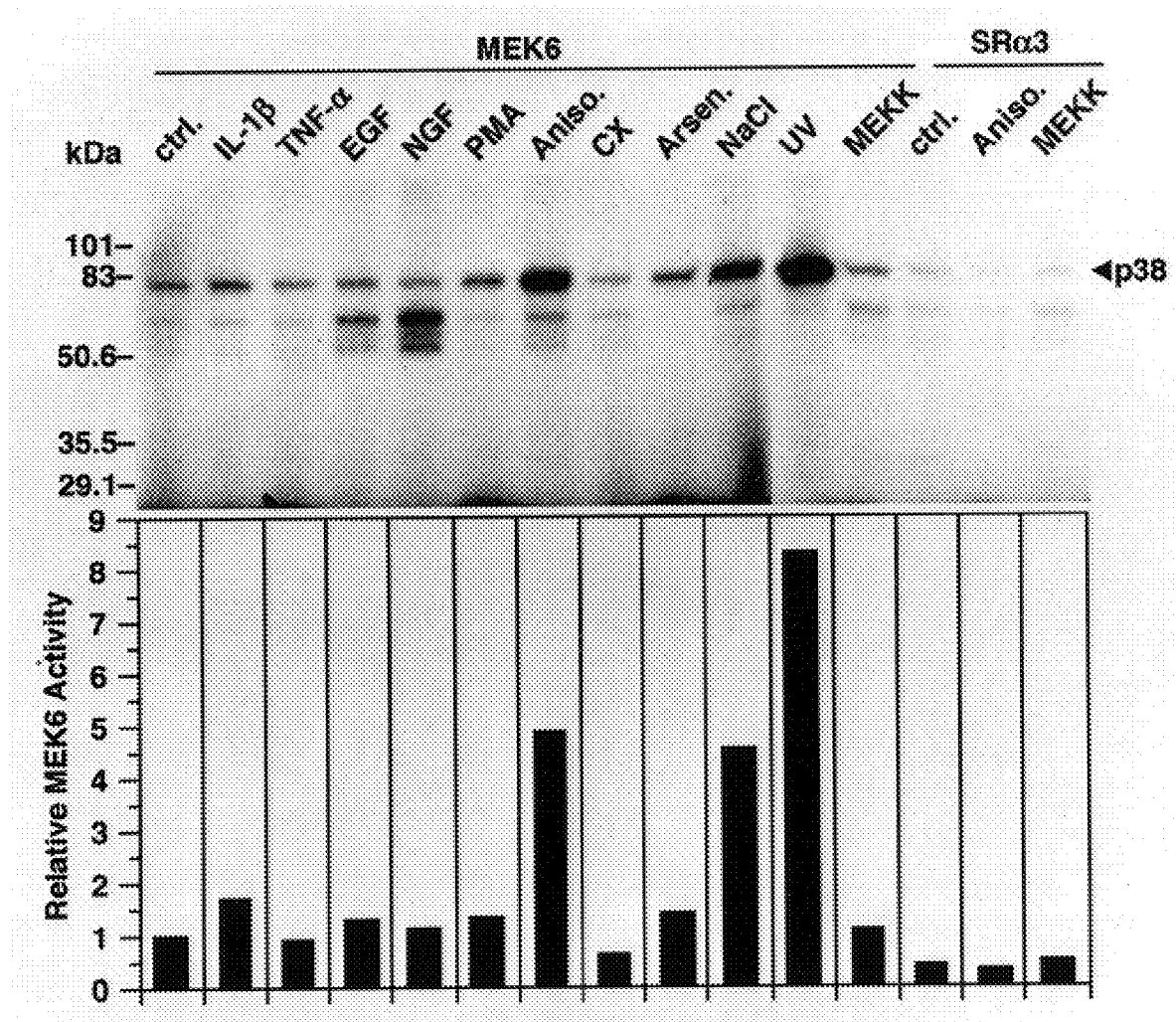
FIGS. 7A and 7B are autoradiograms and graphs showing the relative levels of MEK6 kinase activity in HeLa cells (FIG. 7A) or COS cells (FIG. 7B) transiently transfected with epitope-tagged MEK6 (lanes 1 to 12) or the empty expression vector SRα3 (lanes 13 to 16) and treated for 45 min with IL-1β (10 ng/ml), TNF-α (10 ng/ml), EGF (50 ng/ml), NGF (50 ng/ml), PMA (50 ng/ml), Anisomycin (50 ng/ml), Cycloheximide (CX, 50 ng/ml), Arsenite (200 μM), NaCl (200 μM) or UV (254 nm; 120 J/m$^2$) or cotransfected with 1000 ng CMV5-MEKK as indicated. The position of protein molecular weight markers in kDa is illustrated on the left. MEK6 activity depicted in the graphs was quantitated with a phosphorimager and ImageQuant software.

To investigate the pattern of regulation of MEK6, cells were transiently transfected with 3×HA-MEK6 (as described in Example 3) and treated with various stimulators of the MAPK pathway. In HeLa cells strongest inducers of MEK6 were UV, anisomycin and NaCl followed by weak induction with IL-1β (FIG. 7A). NGF and EGF, two strong inducers of the ERK pathway, did not activate MEK6 although we noted the inducible phosphorylation of two lower molecular weight bands (see discussion).

Figure 7B:
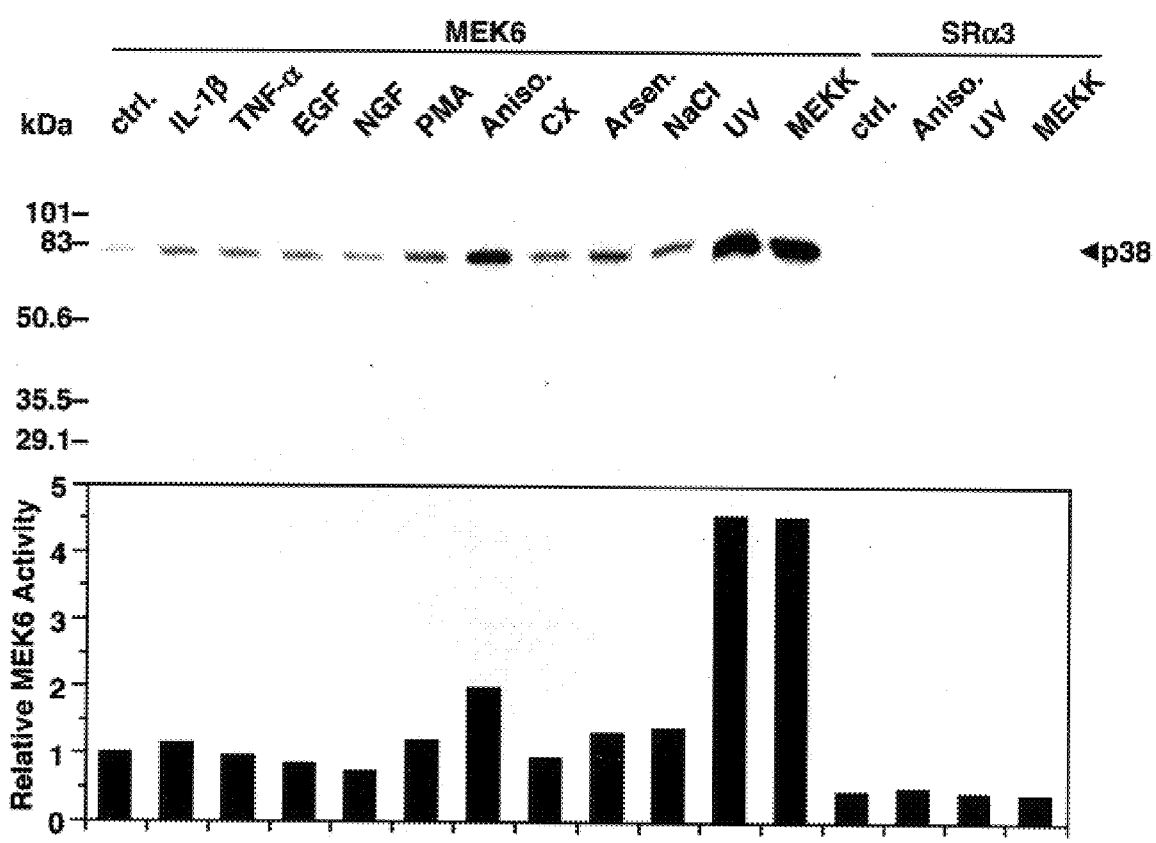

Similar experiments were performed in COS cells, which were transfected by the DEAE-Dextran method (Kawai and Nishizawa, *Mol. Cell. Biol.* 4:1172–1174 (1984)). These experiments showed a strong induction of MEK6 by UV and to a lesser extent by anisomycin (FIG. 7B). MEK6 was present at equal levels in all kinase reactions as determined by Western Blot analysis (data not shown).

These results demonstrate that MEK6 is strongly activated by stress-inducing and DNA-damaging agents, anisomycin, UV and also by osmotic shock. Phorbol esters, NGF and EGF, strong stimulators of the ERK pathway did not stimulate MEK6. Similarly, cycloheximide, a stimulator of p54 kinase and of the ERK pathway, did not significantly activate MEK6. Interestingly, we noted in our in vivo kinase assays with lysates prepared from HeLa cells, but not from COS cells, two bands of variable intensity that were stimulated by NGF and EGF. These bands most likely represent contaminants of the immunoprecipitation phosphorylated by ERK family members.

Example 5

MEK6 is Not a Physiological Substrate for MEKK

This Example evaluates the ability of MEKK to phosphorylate MEK6 as compared to its ability to phosphorylate JNKK.

MEKK has been described as a MAPKKK leading to the phosphorylation and activation of JNKK (Lin et al., *Science* 268:286–290 (1995); Minden et al., *Science* 266:1719–1722 (1994); Yan et al., *Nature* 372:798–800 (1994)). In an initial experiment, HeLa (FIG. 7A) or COS (FIG. 7B) cells were transiently transfected with epitope-tagged MEK6 (lanes 1 to 12) or the empty expression vector SRα3 (lanes 13 to 16) and treated for 45 min with IL-1β (10 ng/ml), TNF-β (10 ng/ml), EGF (50 ng/ml), NGF (50 ng/ml), PMA (50 ng/ml), Anisomycin (50 ng/ml), Cycloheximide (CX, 50 ng/ml), Arsenite (200 μM), NaCl (200 μM), UV (254 nm; 120 J/m$^2$) or cotransfected with 1000 ng CMV5-MEKK as indicated. Cell lysates were used in an immune complex kinase assay with GST-p38 substrate as described in Example 3. MEK6 activity was quantitated with a phosphorimager and ImageQuant software. The presence of equal amounts of MEK6 in all kinase reactions was confirmed by Western blot analysis (data not shown).

Figure 8:
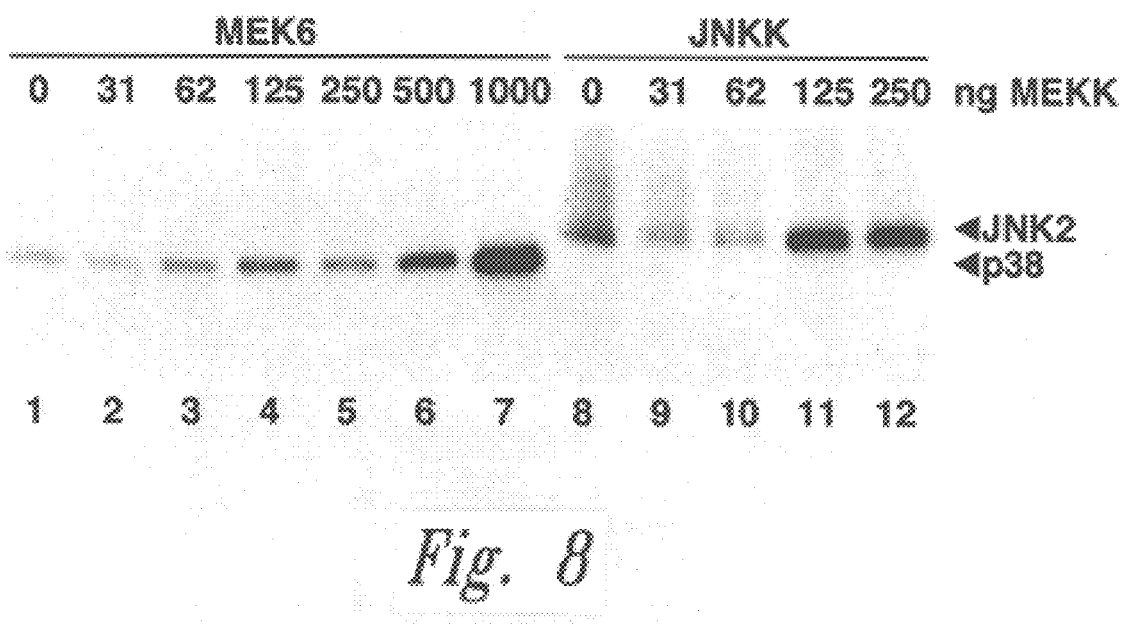
FIG. 8 is an autoradiogram showing the relative levels of MEK6 kinase activity in COS cells transiently transfected with epitope-tagged MEK6 (lanes 1 to 7) or JNKK (lanes 8 to 12) and increasing amounts of CMV5-MEKK expression vector as indicated. The position of protein molecular weight markers in kDa is illustrated on the left. The position of p38 and JNK2 is indicated on the right.

With 1000 ng cotransfected expression vector for MEKK, we observed stimulation of MEK6 activity in COS cells but not HeLa cells (FIG. 7A, lane 12, FIG. 7B, lane 12). This prompted us to examine more carefully whether MEKK is able to phosphorylate MEK6. COS cells were transiently transfected with increasing amounts of expression vector encoding MEKK in the presence of a constant amount of expression vector encoding epitope-tagged MEK6 (FIG. 8, lanes 1 to 7) or JNKK (FIG. 8, lanes 8 to 12), and increasing amounts of CMV5-MEKK expression vector as indicated in FIG. 8. Cell lysates were used in an immune complex kinase assay with GST-p38 (lanes 1 to 7) or GST-JNK2 (lanes 8 to 12) substrate as described in Example 3. Kinase activity was quantitated with a phosphorimager and ImageQuant software.

We observed strong JNKK activation in cells transfected with as little as 125 ng of the MEKK expression vector. Comparable amounts of MEK6 activation, however, were not observed until 1000 ng of the MEKK expression vector were cotransfected. These data suggest that MEKK does not participate in the kinase cascade consisting of MEK6 and p38.

From the foregoing, it will be appreciated that, although specific embodiments of the invention have been described herein for the purpose of illustration, various modifications may be made without deviating from the spirit and scope of the invention.

We claim:

1. A constitutively active variant of a polypeptide that stimulates p38 phosphorylation, said polypeptide comprising the amino acid sequence provided in SEQ ID NO:2, wherein the variant differs from the sequence provided in SEQ ID NO:2 in one or more conservative substitutions, deletions and/or additions at no more than 10% of the amino acid residues, wherein the variant contains an amino acid substitution at $Lys^{69}$ of SEQ ID NO:2, and wherein the ability of the variant to stimulate p38 phosphorylation is not diminished relative to that of a polypeptide comprising the amino acid sequence provided in SEQ ID NO:2.

2. A polypeptide comprising a sequence that differs from the amino acid sequence provided in SEQ ID NO:2 in substitutions, deletions and/or additions at no more than 10% of the amino acid residues within SEQ ID NO:2, such that said polypeptide is rendered constitutively inactive with respect to its ability to stimulate p38 phosphorylation, wherein the polypeptide contains an amino acid substitution at $Ser^{207}$ or $Thr^{211}$ of SEQ ID NO:2.

* * * * *